(12) United States Patent
Adelman et al.

(10) Patent No.: US 7,989,468 B2
(45) Date of Patent: Aug. 2, 2011

(54) METHODS OF USING SNS-595

(75) Inventors: Daniel C. Adelman, Redwood City, CA (US); Jeffrey A. Silverman, Burlingame, CA (US)

(73) Assignee: Sunesis Pharmaceuticals, Inc., South San Francisco, CA (US)

(*) Notice: Subject to any disclaimer, the term of this patent is extended or adjusted under 35 U.S.C. 154(b) by 730 days.

(21) Appl. No.: 11/080,283

(22) Filed: Mar. 14, 2005

(65) Prior Publication Data
US 2005/0203120 A1 Sep. 15, 2005

Related U.S. Application Data

(60) Provisional application No. 60/553,578, filed on Mar. 15, 2004.

(51) Int. Cl.
*A61K 31/47* (2006.01)
(52) U.S. Cl. ...................................... 514/300
(58) Field of Classification Search .................. 514/300
See application file for complete search history.

(56) References Cited

U.S. PATENT DOCUMENTS

| | | | |
|---|---|---|---|
| 5,078,996 A | 1/1992 | Conlon, III et al. | |
| 5,817,669 A | 10/1998 | Tomita et al. | 514/300 |
| 2003/0216316 A1 | 11/2003 | Haran-Ghera et al. | |
| 2008/0063642 A1 | 3/2008 | Adelman et al. | |

FOREIGN PATENT DOCUMENTS

| | | |
|---|---|---|
| JP | 09-221424 | 8/1997 |
| JP | 11-349565 | 12/1999 |
| WO | WO 01/74395 | 10/2001 |
| WO | WO2005/089756 A1 | 9/2005 |
| WO | WO 2007/028171 | 3/2007 |
| WO | WO 2007/146335 | 12/2007 |
| WO | WO 2008/016678 | 2/2008 |
| WO | WO 2009/054935 | 4/2009 |
| WO | WO 2009/075841 | 6/2009 |

OTHER PUBLICATIONS

The Oxford Textbook of Oncology, 1995, vol. 1, Oxford University Press, pp. 445-452.*
Freireich et al. Cancer Chemotherapy Reports, 1966, vol. 50, No. 4, pp. 219-244.*
Rustum et al. Pharmac. Ther., 1992, vol. 56, pp. 307-321.*
Tomitra, Kyoji Synthesis and Structure-Activity Relationships of Novel 7-Substituted 1,4-Dihydro-4-oxo-1-(2-thiazolyl)-1,8-naphthyridine-3-carboxylic Acids as Antitumor Agents. Part 1, J. Med. Chem. 2002, vol. 45, pp. 5564-5575, 2002.
Tsuzuki, Yasunori et al., "Efficient stereospecific synthesis of (S,S)-3-methoxy-4-methylaminopyrrolidine", Tetrahedron: Asymmetry, vol. 12, pp. 1793-1799, 2001.
Tsuzuki, Yasunori et al., Synthesis and Structure-Activity Relationships of Novel 7-Substituted 1,4-Dihydro-4-oxo-1-(2-thiazolyl)-1,8-naphthyridine-3-carboxylic Acids as Antitumor Agents. Part 2, vol. 47, pp. 2097-2109, 2004.

Patrick Therasse, et al. "New Guidelines to Evaluate the Response to Treatment in Solid Tumors", Journal of the National Cancer Institute, vol. 92, No. 3, Feb. 2, 2000.
K. Tomtia, et al., Database CAPLUS Accession No: 1999:92763, "Synthesis and Antitumor activity of Novel 7-Substituted 1,4-dihydro-4-oxo-1-2(2-thiazolyl)-1, 8-naphthyridine-3-carobxylic Acids", BK Abstracts, 217th ACS Nat Mtg., Mar. 21-25, 1999.
Shigeki Kashimoto, et al., Database BIOSIS Accession No: 2001:366681, "Antitumor Activity of a Novel Quinolone Analog AG-7352 in Human Xenograft Models of Leukemia or Drug-Resistant Tumors and in an Experimental Metastatic Tumor Model", Proc. Am. Assoc. Can. Res. An. Mtg., vol. 42, p. 102, Mar. 2001.
T.S. Herman, et al., Database MEDLINE Accession No: 78104303,"Nabilone: A Potent Antiemetic Cannabinol with Minimal Euphoria", Biomedicine, vol. 27, No. 9-10, pp. 331-334, Dec. 1977.
J.C. Allen, Database MEDLINE Accession No. 92345081, "Complications of Chemotherapy in Patients with Brain and Spinal Cord Tumors", Ped. Neurosurg., vol. 17, No. 4, pp. 218-224, 1991-1992.
B. Ryffel, Database CANCERLIT Accession No. 97254190, "Safety of Human Recombinant Proteins", Biomed. Environ. Sci. vol. 10, No. 1, pp. 65-72, Mar. 1997.
J. Glaspy, et al., Database CANCERLIT Accession No. 2002-047630, "A Dose-Finding and Safety Study of Novel Erythropoiesis Stimulating Protein (NESP) for the Treatment of Anaemia in Patients Receiving Multicycle Chemotherapy", Br. J. Cancer, vol. 84 (Suppl. 1), pp. 17-23, Apr. 2001.
Anthony W. Tolcher, et al., "Phase I and Pharmacokinetic Study of NSC 655649, a Rebeccamycin Analog with Topoisomerase Inhibitory Properties", Journal of Clinical Oncology, vol. 19, No. 11, Jun. 1, 2001.
Chiba, et al., "Practical Synthesis of AG-7352, Optically Active New Antitumor Agent." Abstract, 218th ACS National Meeting, Aug. 22-26, 1999.
Evanchik, et al., "Non-Clinical Admet, PK, and Biological Activity of SNS-595, a Novel Cell Cycle Inhibitory Antineoplastic Agent." Drug metabolism reviews, Marcel Dekker,New York, NY, US, vol. 36, No. SUPPL1, Aug. 2004 (2004-2008), p. 103. XP008073741.
Lawrence, et al., "SNS-595, a Novel S-Phase Active Cytotoxic, Demonstrates Pharmacologic Properties Appropriate for the Treatment of Advanced Hematologic Malignancies." Blood, vol. 106, No. 11, Part 2, Nov. 2005, p. 2378. XP008073743.
Lawrence, et al., "SNS-595, A Novel S-Phase Active Cytotoxic, Exhibits Potent In Vitro and In Vivo Activities, and Has the Potential for Treating Advanced Hematoloic Malignacies." Proceedings of the Annual Meeting of the American Association for Cancer Research, New York, NY, vol. 47, Apr. 2006, p. 1110. XP001199684.
Nakano, et al., "Antitumor Activity of a Novel Quinolone DNA Topoisomerase II Inhibitor AG-7352." Proceedings of the Annual Meeting of the American Association for Cancer Research, New York, NY, vol. 40, Mar. 1999, p. 115-Abstract 767. XP008073720.
Sato, et al., "In Vivo Antitumor Activity of a Novel Quinolone Analogue AG-7352 Against a Borad-Spectrum of Cancers and Drug-Resistant Human Cancers." Abstract, 11th NCI-EOARTC-AACR symposium on new drugs in cancer therapy, Nov. 7-10, 2000.
Tsuyuki, et al., "Practical Synthesis of (3S,4S)-3-Methoxy-4-Methylaminopyrrolidine." Tetrahedron: Asymmetry 12(2001) 2989-2997.

(Continued)

Primary Examiner — James Anderson
(74) Attorney, Agent, or Firm — Jones Day

(57) ABSTRACT

The present invention relates to SNS-595 and methods of treating cancer using the same.

43 Claims, 1 Drawing Sheet

OTHER PUBLICATIONS

Tsuzuki, et al., "Process Research of a Novel Quinolone Antitumor Agent, AG-7352." English Abstract, The Japanese Society for Process Chemstry, 2004 Summer Symposium.

Tsuzuki, et al., "Synthesis and Structure—Activity Relationships of 3-Substitued 1, 4-Dihydro-4-Oxo-1-(2-Thiazolyl)-1, 8-Naphthridines as Novel Antitumor Agents." Bioorganic & Medicinal Chemistry Letters 14 (2004): 3189-3193.

Tsuzuki, et al., "Synthesis of Optically Active Amine at C-7 Position of New Antitumor Agent AG-7352." Abstract, Molecular Chirality Conference, 1999.

Wright, et al., "SNS-595 Has Synergistic Activity in Vitro with DNA Damaging Agents and Antimetabolites." Proceddings of the Annual Meeting of the American Association for Cancer Research, New York, NY, vol. 47, Apr. 2006, p. 504.

* cited by examiner

METHODS OF USING SNS-595

This application claims priority to U.S. Ser. No. 60/553,578 filed Mar. 15, 2004 and is incorporated herein by reference.

SNS-595 is novel naphthyridine cytotoxic agent that was previously known as AG-7352 (see e.g., Tsuzuki et al., *Tetrahedron-Asymmetry* 12: 1793-1799 (2001) and U.S. Pat. No. 5,817,669). The chemical name of SNS-595 is (+)-1,4-dihydro-7-[(3S,4S)-3-methoxy-4-(methylamino)-1-pyrrolidinyl]-4-oxo-1-(2-thiazoyl)-1,8-naphthyridine-3-carboxylic acid and has the structure shown below

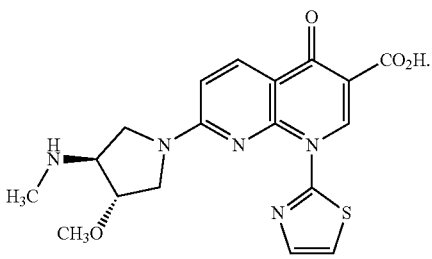

The present invention relates to pharmaceutical compositions and methods of using SNS-595 to treat cancer.

DETAILED DESCRIPTION

Figure 1:
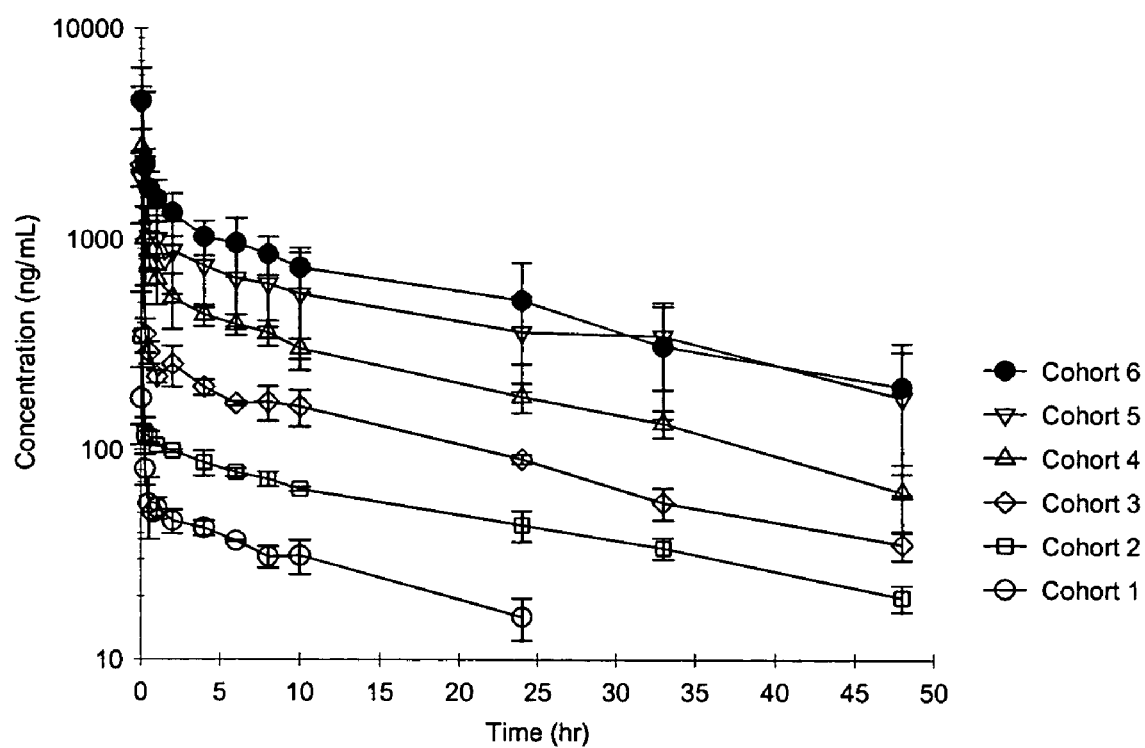
FIG. 1 depicts the plasma concentrations of SNS-595 over time among the various patient cohorts.

In one aspect of the present invention, pharmaceutical composition is provided comprising:
a) SNS-595 and
b) an acid
in an aqueous solution wherein the pH of the solution is 2-3.5. As used herein, a numerical range is intended to be inclusive. For example, the range of pH 2-3.5 includes both pH 2 and pH 3.5. In one embodiment, the pH of the composition is 2-3. In another embodiment, the pH of the composition is 2.3-2.7. As used herein, an aqueous solution is a liquid comprising water.

Suitable examples of acids include both organic and inorganic acids such as acetic acid, ascorbic acid, benzene-sulfonic acid, ethanesulfonic acid, glycolic acid, hydrogen chloride, hydrogen bromide, hydroxyethanesulfonic acid, lactic acid, maleic acid, methanesulfonic acid, proprionic acid, succinic acid, sulfuric acid, trifluoroacetic acid, and toluenesulfonic acid. In one embodiment, the acid is hydrochloric acid, methanesulfonic acid or lactic acid. In another embodiment, the acid is methanesulfonic acid.

In another embodiment, the pharmaceutical composition further comprises a tonicity agent. Suitable examples of a tonicity agent include amino acids (e.g., alanine and glycine), electrolytes (e.g., sodium chloride and potassium chloride), monosaccharides (e.g. glucose or galactose), disaccharides (e.g. sucrose) and hexahydric alcohols (e.g., mannitol and sorbitol). In another embodiment, the tonicity agent is sodium chloride, glucose, mannitol, or sorbitol. In another embodiment, the tonicity agent is a hexahydric alcohol. In another embodiment, the tonicity agent is sorbitol.

SNS-595 is a cytotoxic agent for the treatment of cancer. The types of cancers that can be treated using the inventive methods include but are not limited to: bladder cancer, breast cancer, cervical cancer, colon cancer (including colorectal cancer), esophageal cancer, head and neck cancer, leukemia, liver cancer, lung cancer (both small cell and non-small cell), lymphoma, melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer.

In another aspect of the invention, a method of using SNS-595 to treat a human cancer is provided. The method comprises administering to a patient on the basis of body surface area, a dose of 10 mg/m$^2$-150 mg/m$^2$ of SNS-595. Body surface area calculations can be calculated for example, with the Mosteller formula wherein:

$BSA$ (m$^2$)=square root of [(height(cm)×weight (kg)/3600].

In another embodiment, the dose is 10 mg/m$^2$-100 mg/m$^2$. In another embodiment, the dose is 30 mg/m$^2$-75 mg/m$^2$. In another embodiment, the dose is 40 mg/m$^2$-80 mg/m$^2$. In another embodiment, the dose is 50 mg/m$^2$-90 mg/m$^2$.

In another embodiment the dose is 20 mg/m$^2$-30 mg/m$^2$. In another embodiment the dose is 25 mg/m$^2$-35 mg/m$^2$. In another embodiment the dose is 40 mg/m$^2$-50 mg/m$^2$. In another embodiment the dose is 45 mg/m$^2$-55 mg/m$^2$. In another embodiment the dose is 50 mg/m$^2$-60 mg/m$^2$. In another embodiment the dose is 55 mg/m$^2$-65 mg/m$^2$. In another embodiment the dose is 60 mg/m$^2$-70 mg/m$^2$. In another embodiment the dose is 65 mg/m$^2$-75 mg/m$^2$. In another embodiment the dose is 70 mg/m$^2$-80 mg/m$^2$. In another embodiment the dose is 75 mg/m$^2$-85 mg/m$^2$. In another embodiment the dose is 80 mg/m$^2$-90 mg/m$^2$. In another embodiment the dose is 85 mg/m$^2$-95 mg/m$^2$. In another embodiment the dose is 90 mg/m$^2$-100 mg/m$^2$.

In another embodiment the dose is 95 mg/m$^2$-105 mg/m$^2$. In another embodiment the dose is 100 mg/m$^2$-110 mg/m$^2$. In another embodiment the dose is 105 mg/m$^2$-115 mg/m$^2$. In another embodiment the dose is 110 mg/m$^2$-120 mg/m$^2$. In another embodiment the dose is 115 mg/m$^2$-125 mg/m$^2$. In another embodiment the dose is 120 mg/m$^2$-130 mg/m$^2$. In another embodiment the dose is 125 mg/m$^2$-135 mg/m$^2$. In another embodiment the dose is 130 mg/m$^2$-140 mg/m$^2$. In another embodiment the dose is 135 mg/m$^2$-145 mg/m$^2$. In another embodiment the dose is 140 mg/m$^2$-150 mg/m$^2$.

The administered dose of SNS-595 can be delivered simultaneously (e.g. a single bolus injection) or over a 24-hour period (e.g., continuous infusion over time or divided bolus doses over time) and is repeated until the patient experiences stable disease or regression, or until the patient experiences disease progression or unacceptable toxicity. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The administered dose of SNS-595 can be expressed in units other than as mg/m$^2$. For example, doses can be expressed as mg/kg. One of ordinary skill in the art would readily know how to convert doses from mg/m$^2$ to mg/kg to given either the height or weight of a subject or both (see e.g., http:///www.fda.gov/cder/cancer/animalframe.htm). For example, a dose of 10 mg/m$^2$-150 mg/m$^2$ for a 65 kg human is approximately equal to 0.26 mg/kg-3.95 mg/kg.

In another aspect of the present invention, SNS-595 is administered according to a dosing schedule. In one embodiment, the method comprises:

i) administering a dose of 10 mg/m²-150 mg/m² of SNS-595 to a patient;

ii) waiting a period of at least one day where the subject is not administered any SNS-595;

iii) administering another dose of 10 mg/m²-150 mg/m² of SNS-595 to the patient; and, iv) repeating steps ii)-iii) a plurality of times.

For example, if the waiting period were 6 days, then the initial dose of SNS-595 is administered on Day 1 (step i); the waiting period is six days (step ii); and the following dose of SNS-595 is administered on Day 8 (step iii). Other exemplary time periods include 2 days, 3 days, 13 days, 20 days, and 27 days. In another embodiment, the waiting period is at least 2 days and steps ii) through iii) are repeated at least three times. In another embodiment, the waiting period is at least 3 days and steps ii) through iii) are repeated at least five times. In another embodiment, the waiting period is at least 3 days and steps ii) through iii) are repeated at least three times. In another embodiment, the waiting period is at least 3 days and steps ii) through iii) are repeated at least five times. In another embodiment, the waiting period is at least 6 days and steps ii) through iii) are repeated at least three times. In another embodiment, the waiting period is at least 6 days and steps ii) through iii) are repeated at least five times. In another embodiment, the waiting period is at least 20 days and steps ii) through iii) are repeated at least three times. In another embodiment, the waiting period is at least 20 days and steps ii) through iii) are repeated at least five times. In another embodiment, the waiting period is at least 27 days and steps ii) through iii) are repeated at least three times. In another embodiment, the waiting period is at least 27 days and steps ii) through iii) are repeated at least five times.

In another embodiment, the dosing method comprises administering a weekly dose of SNS-595 to a subject. In another embodiment, the dosing method comprises administering a dose of SNS-595 to a subject every two weeks. In another embodiment, the dosing method comprises administering a dose of SNS-595 to a subject every three weeks. In another embodiment, the dosing method comprises administering a dose of SNS-595 to a subject every four weeks.

In another embodiment, the dosing method comprises a cycle wherein the cycle comprises administering a dose of SNS-595 to a subject every week for three weeks followed by a period of at least two weeks where no SNS-595 is administered to said subject and wherein the cycle is repeated a plurality of times. In another embodiment, the period where no SNS-595 is administered is two weeks. In another embodiment, the period where no SNS-595 is administered is three weeks.

In another aspect of the invention, a method of treating a solid tumor is provided. The method comprises:

i) administering a dose of 10 mg/m²-100 mg/m² of SNS-595 to a patient;

ii) waiting a period of at least six days where the subject is not administered any SNS-595;

iii) administering another dose of 10 mg/m²-100 mg/m² of SNS-595 to the patient; and, iv) repeating steps ii)-iii) a plurality of times.

In another aspect of the invention, a method of treating a hematologic cancer such as leukemias and lymphomas is provided. The method comprises:

i) administering a dose of 60 mg/m²-150 mg/m² of SNS-595 to a patient;

ii) waiting a period of at least two days where the subject is not administered any SNS-595;

iii) administering another dose of 60 mg/m²-150 mg/m² of SNS-595 to the patient; and, iv) repeating steps ii)-iii) a plurality of times.

In another aspect of the present invention, a method is provided supportive care to patients being treated with SNS-595. The method comprises:

a) administering to a patient a dose of 10 mg/m²-150 mg/m² of SNS-595 and b) administering a therapeutically effective amount of a supportive care agent.

The supportive care agent is any substance that prevents or manages an adverse effect from SNS-595 treatment and is administered according to the appropriate dosing regimen for that substance. For example, different supportive care agents for treating nausea have different dosing regimen. While some are administered prophylactically, others are co-administered with SNS-595 while still others are administered after the administration of SNS-595. Illustrative examples of supportive care agents their doses and dosing regimens are found in The Physician's Desk Reference.

In one embodiment, the supportive care agent is an antiemetic. Illustrative examples of antiemetics include but are not limited to phenothiazines, butyrophenones, benzodiazapines, corticosteroids, serotonin antagonists, cannabinoids, and $NK_1$ receptor antagonists. Examples of phenothiazine antiemetics include prochlorperazine and trimethobenzamide. An example of a butyrophenone antiemetic is haloperidol. An example of a benzodiazapine antiemetic is lorazepam. An example of a corticosteroid antiemetic is dexamethasone. Examples of a serotonin antagonist antiemetic include ondansetron, granisetron, and dolasetron. An example of a cannabinoid antiemetic is dronabinol. An example of an NK1 receptor antagonist is aprepitant.

In another embodiment, the antiemetic is prochlorperazine. In another embodiment, the antiemetic is prochlorperazine and the therapeutically effective amount is 10 mg. In another embodiment, the antiemetic is prochlorperazine and the therapeutically effective amount is an oral dose of 10 mg before the administration of SNS-595. In another embodiment, the antiemetic is prochlorperazine and the therapeutically effective amount is an oral dose of 10 mg every four to six hours as needed after the administration of SNS-595.

In another embodiment, the antiemetic is dexamethasone. In another embodiment, the antiemetic is dexamethasone and the therapeutically effective amount is at least 4 mg. In another embodiment, the antiemetic is dexamethasone and the therapeutically effective amount is an oral dose of 4 mg before the administration of SNS-595. In another embodiment, the antiemetic is dexamethasone and the therapeutically effective amount is an oral dose of 8 mg before the administration of SNS-595. In another embodiment, the antiemetic is dexamethasone and the therapeutically effective amount is an intravenous dose of between about 10 mg and about 20 mg before the administration of SNS-595. In another embodiment, the antiemetic is dexamethasone and the therapeutically effective amount is an oral dose of 4 mg every six to twelve hours as needed after the administration of SNS-595.

In another embodiment, the antiemetic is lorazepam. In another embodiment, the antiemetic is lorazepam and the therapeutically effective amount is 1 mg. In another embodiment, the antiemetic is lorazepam and the therapeutically effective amount is an oral dose of 1 mg before the administration of SNS-595. In another embodiment, the antiemetic is lorazepam and the therapeutically effective amount is an intravenous dose of 1 mg before the administration of SNS-595. In another embodiment, the antiemetic is lorazepam and the therapeutically effective amount is an oral dose of 1 mg every four to six hours as needed after the administration of SNS-595.

In another embodiment, the antiemetic is dolasetron. In another embodiment, the antiemetic is dolasetron and the therapeutically effective amount is 100 mg. In another embodiment, the antiemetic is dolasetron and the therapeutically effective amount is an oral dose of 100 mg before the administration of SNS-595. In another embodiment, the antiemetic is dolasetron and the therapeutically effective amount is an intravenous dose of 100 mg before the administration of SNS-595.

In another embodiment, the antiemetic is ondansetron. In another embodiment, the antiemetic is ondansetron and the therapeutically effective amount is at least 10 mg. In another embodiment, the antiemetic is ondansetron and the therapeutically effective amount is an intravenous dose of 10 mg before the administration of SNS-595. In another embodiment, the antiemetic is ondansetron and the therapeutically effective amount is an intravenous dose of 32 mg before the administration of SNS-595.

In another embodiment, the antiemetic is granisetron. In another embodiment, the antiemetic is granisetron and the therapeutically effective amount is 10 µg/kg. In another embodiment, the antiemetic is granisetron and the therapeutically effective amount is an intravenous dose of 10 µg/kg before the administration of SNS-595. In another embodiment, the antiemetic is granisetron and the therapeutically effective amount is at least 1 mg. In another embodiment, the antiemetic is granisetron and the therapeutically effective amount is an oral dose of 1 mg before the administration of SNS-595. In another embodiment, the antiemetic is granisetron and the therapeutically effective amount is an oral dose of 2 mg before the administration of SNS-595.

In another embodiment, the antiemetic is aprepitant. In another embodiment, the antiemetic is aprepitant and the therapeutically effective amount is at least 80 mg. In another embodiment, the antiemetic is aprepitant and the therapeutically effective amount is an oral dose of 125 mg before the administration of SNS-595. In another embodiment, the antiemetic is aprepitant and the therapeutically effective amount is a daily oral dose of 80 mg for at least two days after the administration of SNS-595.

In another embodiment, the supportive care agent is a hematopoietic agent. A hematopoietic agent is a molecule that stimulates hematopoiesis. Illustrative examples of hematopoietic agents include but are not limited to granulocyte colony stimulating factor (G-CSF), granulocyte macrophage colony stimulating factor (GM-CSF), erythropoietin and erythropoiesis stimulating protein, and derivatives thereof. Examples of G-CSF include but are not limited to filgrastim and its derivatives including pegfilgrastim. An example of GM-CSF includes sargramostim. An example of erythropoietin is epoetin alfa. An example of erythropoiesis stimulating protein is darbepoetin alfa.

In another embodiment, the hematopoietic agent is G-CSF. In another embodiment, the hematopoietic agent is filgrastim. In another embodiment, the hematopoietic agent is filgrastim and the therapeutically effective amount is at least 4 µg/kg. In another embodiment, the hematopoietic agent is filgrastim and the therapeutically effective amount is a daily dose of at least 4 µg/kg for at least 7 days after the administration of SNS-595. In another embodiment, the hematopoietic agent is filgrastim and the therapeutically effective amount is a daily subcutaneous dose of between about 4 µg/kg and about 8 µg/kg for at least 7 days starting from the third day after the administration of SNS-595. In another embodiment, the hematopoietic agent is filgrastim and the therapeutically effective amount is a daily subcutaneous dose of between about 4 µg/kg and about 10 µg/kg for at least 14 days starting from the third day after the administration of SNS-595.

In another embodiment, the hematopoietic agent is pegfilgrastim. In another embodiment, the hematopoietic agent is pegfilgrastim and the therapeutically effective amount is 6 mg. In another embodiment, the hematopoietic agent is pegfilgrastim and the therapeutically effective amount is a daily subcutaneous dose of 6 mg after the administration of SNS-595. In another embodiment, the hematopoietic agent is pegfilgrastim and the therapeutically effective amount is 100 µg/kg. In another embodiment, the hematopoietic agent is pegfilgrastim and the therapeutically effective amount is a daily dose of 100 µg/kg after the administration of SNS-595.

In another embodiment, the hematopoietic agent is GM-CSF. In another embodiment, the hematopoietic agent is sargramostim. In another embodiment, the hematopoietic agent is sargramostim and the therapeutically effective amount is 250 µg/m$^2$. In another embodiment, the hematopoietic agent is sargramostim and the therapeutically effective amount is a daily intravenous or subcutaneous dose of 250 µg/m$^2$. In another embodiment, the hematopoietic agent is sargramostim and the therapeutically effective amount is a daily intravenous or subcutaneous dose of 250 µg/m$^2$ as needed starting from the third day after the administration of SNS-595. In another embodiment, the hematopoietic agent is sargramostim and the therapeutically effective amount is a daily intravenous or subcutaneous dose of 250 µg/m$^2$ as needed starting from the tenth day after the administration of SNS-595.

In another embodiment, the hematopoietic agent is erythropoietin. In another embodiment, the hematopoietic agent is epoetin alfa. In another embodiment, the hematopoietic agent is epoetin alfa and the therapeutically effective amount is at least 150 units/kg. In another embodiment, the hematopoietic agent is epoetin alfa and the therapeutically effective amount is an intravenous or subcutaneous dose of 150 units/kg three times a week after the administration of SNS-595. In another embodiment, the hematopoietic agent is epoetin alfa and the therapeutically effective amount is an intravenous or subcutaneous dose of 300 units/kg three times a week after the administration of SNS-595. In another embodiment, the hematopoietic agent is epoetin alfa and the therapeutically effective amount is 40,000 units. In another embodiment, the hematopoietic agent is epoetin alfa and the therapeutically effective amount is a weekly dose of 40,000 units after the administration of SNS-595.

In another embodiment, the hematopoietic agent is erythropoiesis stimulating protein. In another embodiment, the hematopoietic agent is darbepoetin alfa. In another embodiment, the hematopoietic agent is darbepoetin alfa and the therapeutically effective amount is between about 1.5 µg/kg and about 4.5 µg/kg. In another embodiment, the hematopoietic agent is darbepoetin alfa and the therapeutically effective amount is a weekly dose of between about 1.5 µg/kg and about 4.5 µg/kg.

All cited references are incorporated herein by reference.

EXAMPLE 1

Pharmaceutical Composition Suitable for Injection or Intravenous Infusion

Acidic compositions (<pH 4) provided the appropriate balance of increased solubility of SNS-595 and desirable pharmaceutical properties (e.g. increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

EXAMPLE 2

Pharmacokinetics of SNS-595 in Cancer Patients

SNS-595 was administered to enrolled patients for up to six cycles. A cycle is defined as a three-week period, with SNS-595 administered on the first day of each cycle (day 0), followed by at least 21 days of observation. SNS-595 was administered to cohorts of at least 3 patients and dose escalation occurred by sequential cohort. Doses of SNS-595 were linear with AUC ∞ and its pharmacokinetic properties were remarkably consistent among patients in the same cohort. FIG. 1 depicts the plasma concentrations of SNS-595 over time among the various patient cohorts and Table 1 shows the pharmacokinetic parameters derived there from.

TABLE 1

| Dose (mg/m2) | HL (hr) | C0 (ng/mL) | Cmax (ng/mL) | AUClast (hr·ng/mL) | AUCINF_obs (hr·ng/mL) | CI_obs (mL/min/kg) | Vz_obs (L/kg) | Vss_obs (L/kg) | MRTINF_obs (hr) |
|---|---|---|---|---|---|---|---|---|---|
| 3 | 16.27 | 152.25 | 138.80 | 750.08 | 1139.55 | 1.14 | 1.55 | 1.44 | 21.96 |
| SD | 4.871 | 82.282 | 80.566 | 87.622 | 263 | 0.318 | 0.297 | 0.277 | 6.836 |
| 6 | 20.69 | 376.69 | 347.00 | 2400.00 | 2990.29 | 0.71 | 1.28 | 1.24 | 29.05 |
| SD | 0.327 | 243.598 | 214.96 | 170.556 | 245.64 | 0.153 | 0.295 | 0.218 | 1.15 |
| 12 | 17.81 | 2888.66 | 2246.67 | 5395.53 | 6329.15 | 0.76 | 1.17 | 1.07 | 23.87 |
| SD | 3.896 | 1302.71 | 1065.145 | 292.281 | 181.804 | 0.126 | 0.258 | 0.184 | 5.021 |
| 24 | 16.14 | 2924.46 | 2703.33 | 11133.03 | 12655.32 | 0.83 | 1.15 | 1.06 | 21.65 |
| SD | 2.601 | 2884.702 | 2573.02 | 468.453 | 851.458 | 0.108 | 0.124 | 0.165 | 5.261 |
| 48 | 21.32 | 1984.52 | 2868.00 | 21098.53 | 27347.36 | 0.99 | 1.57 | 1.46 | 28.90 |
| SD | 6.32 | 189.677 | 2379.899 | 9405.346 | 14382.787 | 0.616 | 0.567 | 0.47 | 8.91 |
| 80 | 17.63 | 4797.47 | 4537.50 | 28112.17 | 33616.18 | 0.83 | 1.20 | 1.08 | 23.71 |
| SD | 4.15 | 2215.20 | 1947.89 | 9127.12 | 13081.44 | 0.352 | 0.37 | 0.218 | 6.93 |

What is claimed is:

1. A method for treating leukemia comprising administering to a human patient having leukemia a dose of about 50-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

2. The method of claim 1 wherein the dose is 50 mg/m$^2$-90 mg/m$^2$.

3. The method of claim 1 wherein the dose is 90 mg/m$^2$-100 mg/m$^2$.

4. The method of claim 1 wherein the does is 100 mg/m$^2$-110 mg/m$^2$.

5. The method of claim 1 additionally comprising administering to said patient a therapeutically effective dose of a supportive care agent.

6. The method of claim 5 wherein the supportive care agent is an antiemetic.

7. The method of claim 5 wherein the supportive care agent is a hematopoietic agent.

8. A method for treating leukemia comprising: i) administering a dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to a human patient having leukemia; ii) waiting a period of at least one day where the patient is not administered any (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid; iii) administering another dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to the patient.

9. The method of claim 8 wherein the period is at least 2 days.

10. The method of claim 8 wherein the period is at least 3 days.

11. The method of claim 8 wherein the period is at least 6 days.

12. The method of claim 8 wherein the period is at least 13 days.

13. The method of claim 8 wherein the period is at least 20 days.

14. The method of claim 8 wherein the period is at least 27 days.

15. A method for treating leukemia comprising administering a weekly dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to a human patient having leukemia.

16. A method for treating leukemia comprising administering a dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid once every three weeks to a human patient having leukemia.

17. A method for treating leukemia comprising a cycle wherein the cycle comprises i) administering a dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid once every week for three weeks to a human patient having leukemia followed by ii) a period of at least two weeks where no (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered to said patient.

18. A method for treating leukemia comprising administering to a human patient a dose of about 50 mg/m$^2$-110 mg/m$^2$ of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and one or more doses of a hematopoietic agent.

19. The method of claim 18 wherein the hematopoietic agent is G-CSF.

20. The method of claim 18 wherein the hematopoietic agent is GM-CSF.

21. The method of claim 18 wherein the hematopoietic agent is erythropoietin.

22. The method of claim 18 wherein the hematopoietic agent is erythropoiesis stimulating protein.

23. The method of claim 18 wherein the hematopoietic agent is darbepoietin alfa.

24. The method of claim 8, wherein the dose is about 50 mg/m$^2$-90 mg/m$^2$.

25. The method of claim 8, wherein the dose is about 90 mg/m$^2$-100 mg/m$^2$.

26. The method of claim 8, wherein the dose is about 100 mg/m$^2$-110 mg/m$^2$.

27. The method of claim 15, wherein the dose is about 50 mg/m$^2$-90 mg/m$^2$.

28. The method of claim 1 wherein the dose is 50 mg/m$^2$-60 mg/m$^2$.

29. The method of claim 1 wherein the dose is 55 mg/m$^2$-65 mg/m$^2$.

30. The method of claim 1 wherein the dose is 60 mg/m$^2$-70 mg/m$^2$.

31. The method of claim 1 wherein the dose is 65 mg/m$^2$-75 mg/m$^2$.

32. The method of claim 8 further comprising repeating steps ii)-iii) a plurality of times.

33. The method of claim 15, wherein the dose is about 90 mg/m$^2$-100 mg/m$^2$.

34. The method of claim 15, wherein the dose is about 100 mg/m$^2$-110 mg/m$^2$.

35. The method of claim 16, wherein the dose is about 50 mg/m$^2$-90 mg/m$^2$.

36. The method of claim 16, wherein the dose is about 90 mg/m$^2$-100 mg/m$^2$.

37. The method of claim 16, wherein the dose is about 100 mg/m$^2$-110 mg/m$^2$.

38. The method of claim 17, wherein the dose is about 50 mg/m$^2$-90 mg/m$^2$.

39. The method of claim 17, wherein the dose is about 90 mg/m$^2$-100 mg/m$^2$.

40. The method of claim 17, wherein the dose is about 100 mg/m$^2$-110 mg/m$^2$.

41. The method of claim 18, wherein the dose is about 50 mg/m$^2$-90 mg/m$^2$.

42. The method of claim 18, wherein the dose is about 90 mg/m$^2$-100 mg/m$^2$.

43. The method of claim 18, wherein the dose is about 100 mg/m$^2$-110 mg/m$^2$.

* * * * *

UNITED STATES PATENT AND TRADEMARK OFFICE
CERTIFICATE OF CORRECTION

| | | |
|---|---|---|
| PATENT NO. | : 7,989,468 B2 | Page 1 of 1 |
| APPLICATION NO. | : 11/080283 | |
| DATED | : August 2, 2011 | |
| INVENTOR(S) | : Adelman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 655 days.

Signed and Sealed this
Fourteenth Day of February, 2012

David J. Kappos
*Director of the United States Patent and Trademark Office*